United States Patent [19]

Nitsch

[11] Patent Number: 5,506,656
[45] Date of Patent: Apr. 9, 1996

[54] METHOD OF AND APPARATUS FOR MEASURING THE OPTICAL DENSITY OF A PHOTOGRAPHIC NEGATIVE

[75] Inventor: Wilhelm Nitsch, Munich, Germany

[73] Assignee: AGFA-Gevaert, AG, Leverkusen, Germany

[21] Appl. No.: 450,400

[22] Filed: May 25, 1995

Related U.S. Application Data

[63] Continuation of Ser. No. 108,024, Aug. 17, 1993, abandoned.

[30] Foreign Application Priority Data

Sep. 11, 1992 [DE]   Germany ........................ 42 30 451.2

[51] Int. Cl.$^6$ ............................................ G03B 27/73
[52] U.S. Cl. ................... 355/38; 355/35; 355/71; 354/227.1
[58] Field of Search ................... 355/35, 36, 37, 355/38, 71; 354/227.1

[56] References Cited

U.S. PATENT DOCUMENTS

| | | | |
|---|---|---|---|
| 4,279,502 | 7/1981 | Thurm et al. ........................... | 355/38 |
| 4,873,546 | 10/1989 | Zahn et al. . | |
| 5,041,869 | 8/1991 | Frich . | |
| 5,162,919 | 11/1992 | Ono ................................... | 355/71 XL |
| 5,175,697 | 12/1992 | Kawagoe et al. ..................... | 364/526 |

*Primary Examiner*—Michael L. Gellner
*Assistant Examiner*—D. P. Malley
*Attorney, Agent, or Firm*—Furgang & Milde

[57] ABSTRACT

A method of and apparatus for measuring the optical density of an original, especially a three-color negative, from which photographic prints are made, to control how much printing light of each color penetrates the original when the image is projected onto a color print medium that is sensitive to these colors. The spectral sensitivity of the measuring apparatus is adjusted to that of the print medium. Measuring light is projected through the original and is resolved into at least one spectrum. The intensities of the light at the various ranges of wavelength are weighted and totaled in accordance with the spectral sensitivity of the particular print medium. Light valves with translucencies that can be adjusted to the sensitivity of the print medium to that range of wavelengths are distributed along the spectrum. The accordingly weighted intensities of the light of each color are separately sensed and measured.

19 Claims, 4 Drawing Sheets

METHOD OF AND APPARATUS FOR MEASURING THE OPTICAL DENSITY OF A PHOTOGRAPHIC NEGATIVE

This application is a continuation of application Ser. No. 108,024, filed Aug. 17, 1993, now abandoned.

BACKGROUND OF THE INVENTION

The present invention concerns a method of measuring the optical density of an original photographic image, and apparatus for carrying out the method, to determine how much printing light of each color penetrates the original when making photographic prints therefrom.

A method and apparatus of this type are described in the German Patent Publication No. OS 3,737,775. Measuring light travels through an original (either a positive or negative) and is resolved into at least one color spectrum by means of a spectroscope. The intensities of the light in the various ranges of wavelength are measured separately. Each result is multiplied by a factor $\Theta_x^{BGR}$ that characterizes the spectral sensitivity of the color print medium at that range to one of the colors red, green, and blue. The totals of the weighted results for each color are employed to determine how much printing light the apparatus will use. Weighing the results for the separate ranges of the spectrum with wavelength-dependent factors theoretically makes it possible to simulate any filter transmission curve. The curves can accordingly be adapted very precisely to the sensitivity of the paper.

The disclosed method, however, does have certain limitations. First, since the light traveling through any area of the original being sensed must be distributed among a large number of light sensitive elements, specifically the pixels of a CCD, each pixel receives only a small amount of light. Secondly, the method demands a relatively long series of calculations, specifically separate multiplication and addition for each individually measured range of the spectrum, to attain corrected brightness levels for each of the three colors at each area of the original.

SUMMARY OF THE INVENTION

The principal object of the present invention is accordingly to provide an improved method and apparatus of the aforesaid type that can detect higher intensities for each pixel and necessitates fewer calculations.

This object, as well as other objects which will become apparent from the discussion that follows, are achieved, in accordance with the present invention, by a method of measuring optical density of an original, such as a photographic negative, and apparatus for carrying out the method, which (1) attenuates light with a plurality of "light valves" that are disposed along the spectrum and controlled in accordance with the sensitivity of the print medium to the respective spectral wavelengths, and (2) measures the resulting weighted intensities of the light at each color that is passed through the light valves.

The translucency of the light valves is adjusted to the spectral sensitivity of the particular color print medium at a specific wavelength range just once, and this setting is retained for all areas of the negative. The various intensities at the spectral plane are thereby weighted in accordance with the print medium's spectral sensitivity, so that only one result must be obtained for the weighted and subsequently collected intensity values of each color. They will accordingly be available at approximately the same outgoing current per photocell as with conventional systems. Since only three measured values have to be processed for each point tested, the expenditures for computing and control are comparable to those of standard, currently available illumination controls. Furthermore, it is no longer necessary to adjust high-precision filters to the spectral sensitivity of each type of paper.

Apparatus for carrying out the aforesaid method is described in detail below.

For a full understanding of the present invention, reference should now be made to the following detailed description of the preferred embodiments of the invention as illustrated in the accompanying drawings.

BRIEF DESCRIPTION OF THE DRAWINGS

FIG. 1b is a block diagram showing a modification of the apparatus of FIG. 1a.

DESCRIPTION OF THE PREFERRED EMBODIMENTS

Figure 1A:
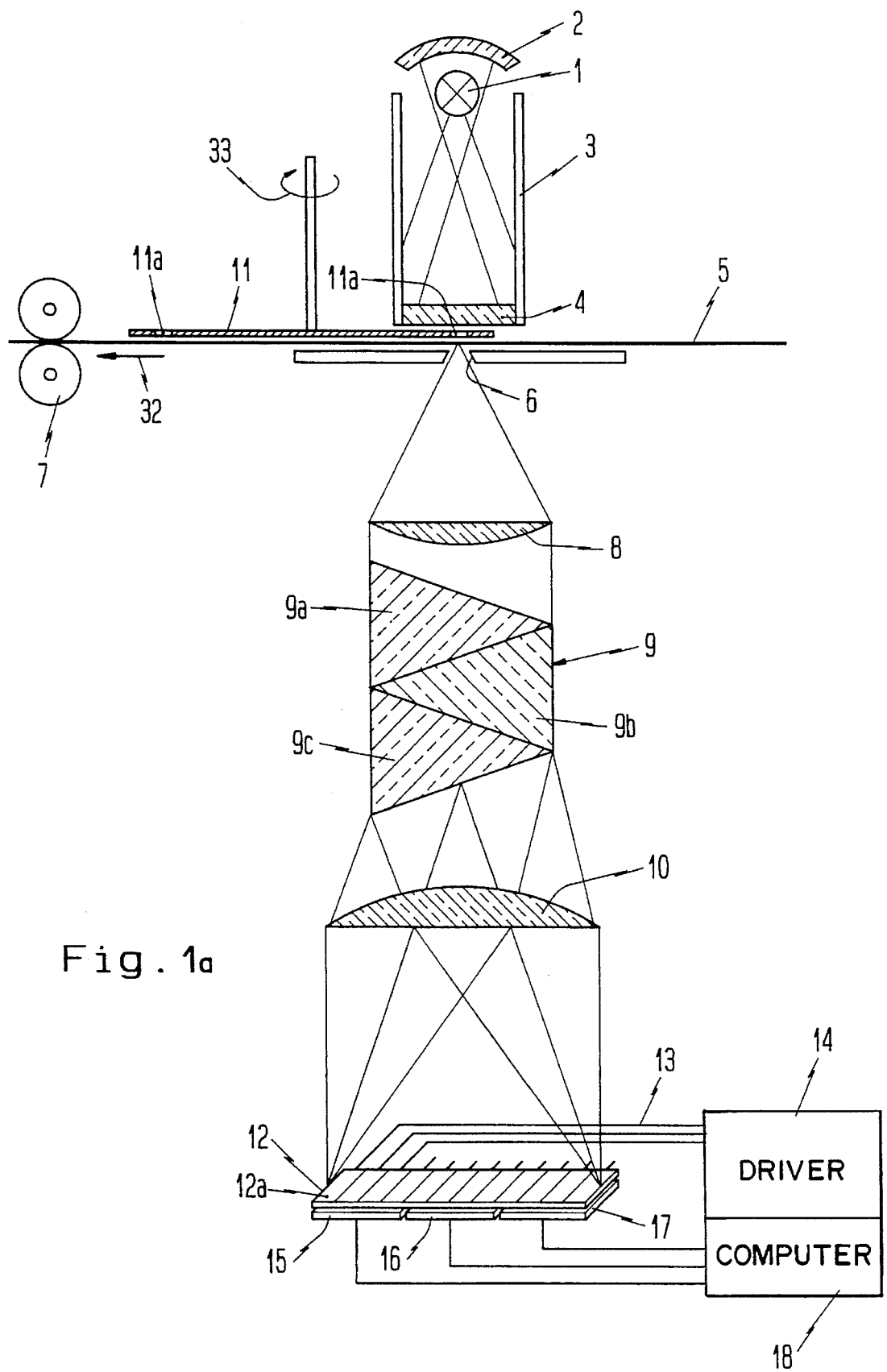
FIG. 1a is a schematic front view of optical density measuring apparatus in accordance with the present invention.

FIG. 1a illustrates an optical density measuring apparatus having an illuminating device that comprises a source 1 of measuring light, a reflector 2, a cylinder 3 with its inner surface silvered, and a ground glass 4. The illuminating device is positioned directly over a film 5 containing several original negatives. Below the film and perpendicular to the direction of film transport indicated by arrow 32 is a slit 6. The slit 6 is demarcated by thin strips of metal limited to the format of the negatives being printed from. Above the slit 6 and between the film 5 and the ground glass 4 is a rotating disk 11 with several radial slots 11a precisely as wide as the areas of the negative being sensed. Rotating the disk in the direction indicated by the arrow 33 will accordingly allow light from the source 1 to travel along the width of film directly above the slit 6 in a succession of points.

The slit 6 is at the focus of a collimator 8, which the light leaving the slit travels through. The collimated beam enters a direct-view prism 9 which is conventionally composed of several subsidiary prisms 9a, 9b and 9c, of different types of glass. Aside from a slight spectral deflection of the center of the beam, the passage of light through the prism 9 is essentially straight through. The light leaving the prism 9 is focussed by a lens 10, producing a sharp image of the slit 6 on photosensors (photocells) 15, 16, and 17. The prism 9 resolves the light, derived from the width of the negative 5 over the slit 6, by wavelength into a spectrum extending along photocells 15, 16, and 17. The blue component of light, for example, can impact photocell 15 at the left and the red can impact photocell 17 on the right. The length of photocells 15, 16, and 17 along the slit 6—i.e., perpendicular to the plane of illustration—corresponds to the width of the negative image.

Above the photocells 15, 16, and 17 is a series 12 of "light valves" 12a which control the amount of light passing through. These light valves can be liquid crystals for example, although other types of devices can also be employed. Each light valve 12a is individually controlled through a separate line 13 by a driver 14. The series 12 of components 12a extends over the same distance (length) in the plane of the illustration as the photocells 15, 16, and 17.

Alternatively, the light valves 12a and photocells 15, 16, and 17 can be divided into a number of partial elements which corresponds to the number of sensing points along the slit 6. In this event the rotating disk 11 becomes unnecessary.

Figure 1B:
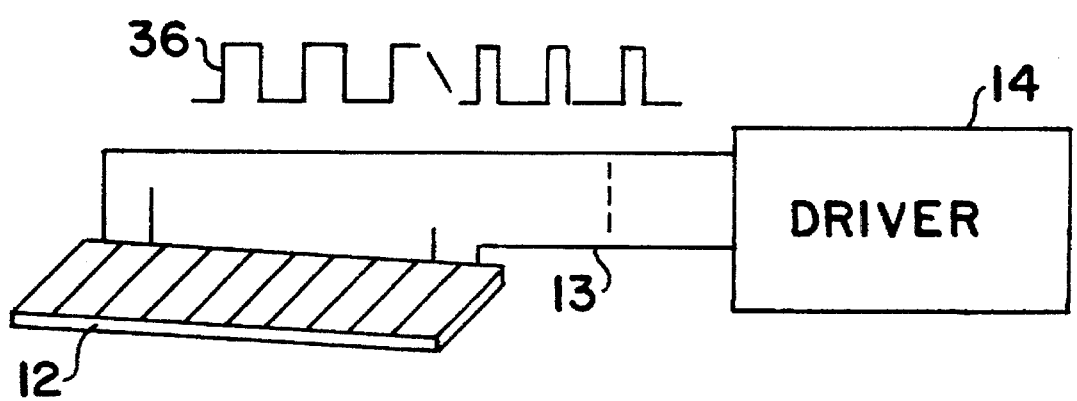
Figure 2A:
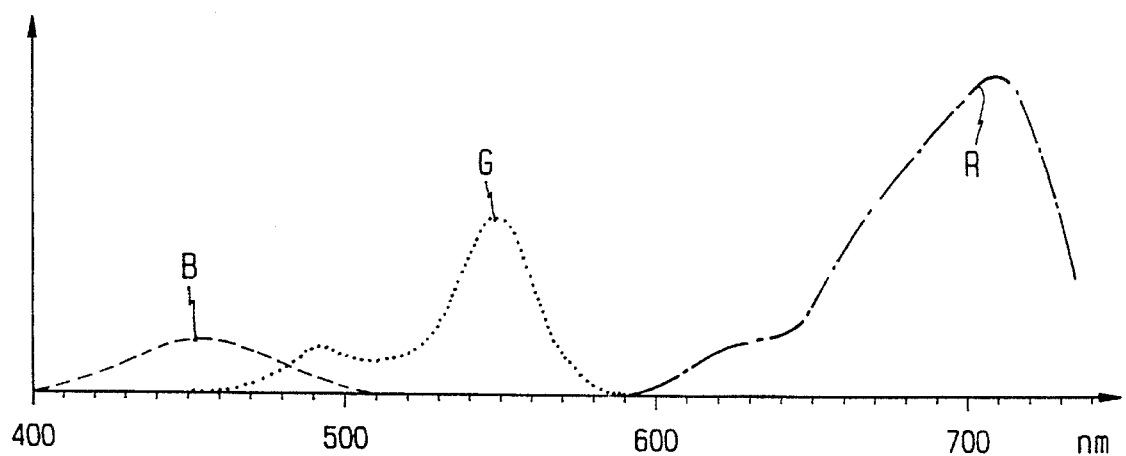
FIG. 2a is a graph representing the color sensitivities of an average color print medium at the wavelength range of 400 to 750 Nm.

FIG. 2a illustrates the spectral sensitivities of the various layers of a color print medium being processed in the apparatus illustrated in FIG. 1 as a function of wavelength. As illustrated by curve B, the blue layer is sensitive to light waves between 400 and 500 Nm long. The green layer, represented by curve G, is sensitive to wavelengths of approximately 460 to 590 Nm. The sensitivity of the red layer, represented by the curve R, extends from 580 to approximately 740 Nm.

The translucencies of the light valves 12a, liquid crystals for example in the series 12, as controlled by the driver 14, are programmed such that the curves of translucency precisely match the curves of sensitivity in FIG. 2a with respect to height and position. The intersections between the photocells 15 and 16 and 16 and 17 are positioned precisely at the points of intersection or contact between the particular curves of sensitivity. This means that the light supplied to the blue photocell can only be evaluated up to a wavelength of approximately 475 Nm and the light for the green photocell from 480 Nm on.

The light valves 12a are narrow enough in width to ensure that the weights they assign to their ranges of the spectrum at mean translucency will eliminate error, even though the cost of providing control for all the individual light valve components is kept within reason.

The operation of the apparatus illustrated in FIG. 1 will now be described.

A film 5 of negatives that are to be used to produce prints is conveyed, one negative at a time, across the slit 6 at such a rate that one of the slots 11a in the disk 11 will sweep all the way along the slit 6 while the film is advanced one slit width. This procedure ensures the complete interpretation of every point in the advance of the light along the slit. The lengths of the photocells 15, 16, and 17 and the liquid-crystal light valves 12a (i.e., in a direction perpendicular to the plane of illustration in FIG. 1) are great enough to ensure that the photocells can effectively sense even the points at the very ends of the slit 6. It is alternatively possible to use a pivoting or polygonal mirror to advance the light, point by point, from the presentation region demarcated by the slit 6 to the spectroscope arrangement 8, 9 and 10. The result in either case is a wavelength total, weighted in accordance with the translucency of each liquid-crystal component 12a in the series 12, for each point on the negative, in each photocell 15, 16 and 17. The levels for the red, green, and blue densities are forwarded through appropriate lines to a processor 18 that operates generally in the manner disclosed in the German Patent No. 2,840,287 (and corresponding U.S. Pat. No. 4,279,502). As described therein, the film travels through rollers 7 at a constant speed while every area thereof, demarcated by a measuring stripe that travels over the film at an angle, is sensed in succession by the photocells 15, 16, and 17. The emergence of one slot 11a at one edge of the film is followed by the coincidence of another slot 11a with slit 6, and the negative, which is being advanced one slit width at a time, is sensed by the next measuring stripe until results for every area of the film are stored in the processor 18.

A series of lenses that project images of the liquid-crystal components 12a onto the photocells 15, 16, and 17 for each color can also be employed instead of positioning the photocells directly below or downstream of these components. When the light penetrates the spectroscope at an angle, or when the spectrum of the light from the source 1 is unevenly distributed and every color in the negative is accordingly not illuminated or evaluated at the same intensity, this situation can be taken into consideration when controlling the translucencies (attenuation) of light valves 12a. Specifically, any irregularities in the wavelength distribution of the measuring light and in the collection of light behind the light valves are compensated by controlling the attenuation of the light valves in accordance with these irregularities. This can be done by a calibration process that involves measuring, adjusting, and storing the intensities of the wavelength ranges associated with all the liquid-crystal pixels with no film at the slit 6. This procedure also takes into account not only the spectral sensitivity of the print medium but also any external interference. A negative is now advanced past the slit 6 to establish the relationship between the intensities with and without the film for all colors as a standard for the transparency of the negative to each color. These results are then converted logarithmically into densities.

Bi-stable liquid-crystal cells (per FIG. 1b) can also be employed instead of the light valves which are continuously controllable by an analog signal (per FIG. 1a) in dependence upon the desired weighting of the intensities of the spectrum. Such bi-stable cells will, like a light shutter, alternate between being completely transparent and completely opaque in response to a pulse train having a duty cycle that depends upon the sensitivity curve. The result is a modulation of translucency with respect to time.

FIG. 1b illustrates a modification of the apparatus of FIG. 1a whereby the light valves are bi-stable liquid-crystal cells that receive pulse trains 36 with variable duty cycles on the respective control lines 13. The amount of light passing through the light valves is thus dependent upon the duty cycles.

Figure 4:
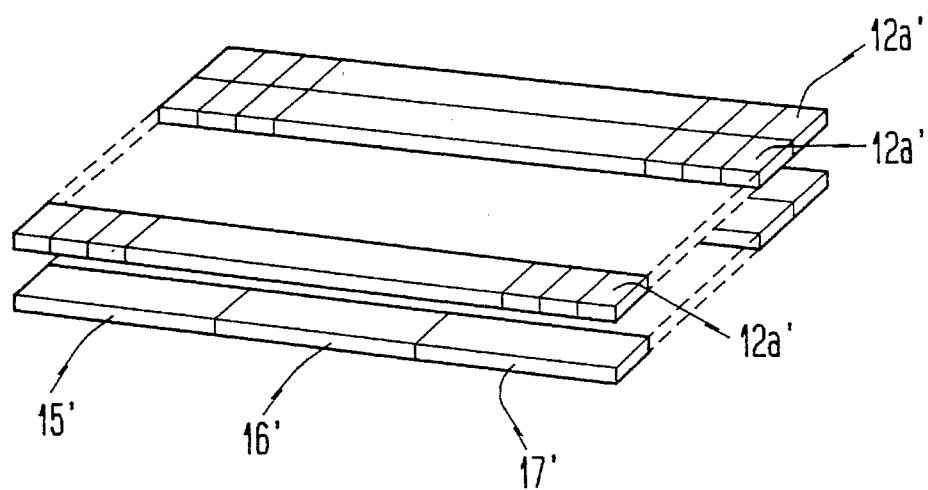
FIG. 4 is a perspective view of a distribution of light valves and photocells with a plurality of light valve rows in accordance with the number of test areas in a slit.

The embodiment illustrated in FIG. 1 can sense only one area of the negative at a time. In the embodiment of FIG. 4, the light valves 12a are distributed along the image of the slit into the same number n of rows of individual controllable subsidiary cells 12a as there are test areas of the negative at the slit 6, for example ten test areas can be sensed for the three colors at once by the ten photocells 15', 16' and 17'.

Figure 2B:
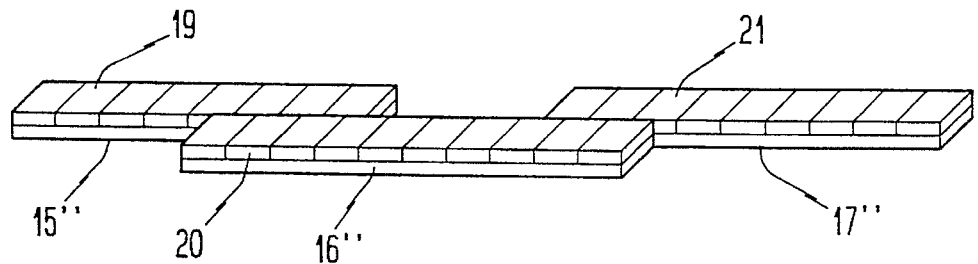
FIG. 2b illustrates the distribution, within the plane of the spectrum of light, of an arrangement of light valves that can be controlled in accordance with the light wavelength.

The overlap of the blue and green curves at 470 to 510 Nm and of the green and red curves in the narrow range around 600 Nm can reduce the accuracy of the evaluation process. This disturbance can be taken into account as illustrated in FIG. 2b by providing a separate row 19, 20, and 21 of liquid-crystal light valves for each color with color-detection photocells 15", 16", and 17" under them, such that the pairs that sense wavelengths in the overlap regions will be next to each other. The distribution within the spectrum being sensed ensures that the cells 19, 20, and 21 will be subject to the lines of the spectrum to the same extent. A total result for each of the three colors will then be available at the photocells 15", 16", and 17" below the rows 19, 20, and 21 of liquid-crystal light valves, the translucencies of which are controlled in accordance with the graph in FIG. 2a.

Figure 3:
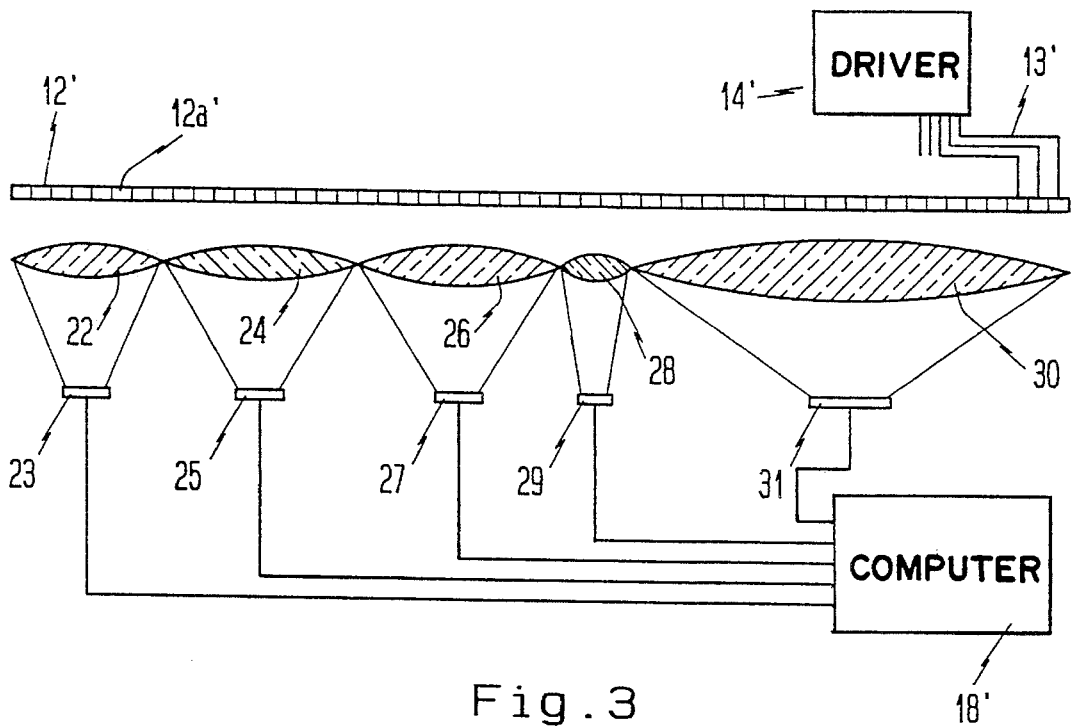
FIG. 3 is a front view of another distribution of light valves and photocells associated with the measuring light spectrum.

Another way of taking into account the overlap of the sensitivity curves in FIG. 2a in determining the results is to provide a single straight row 12' of light valves 12a' as illustrated in FIG. 3. Each valve is controlled by a driver 14' through a line 13' in accordance with the spectral sensitivity illustrated in FIG. 2a. Light valves 12a' are assigned to wavelengths in the manner illustrated in FIG. 2b. Ocular lenses 22, 24, 26, and 28 each produce a continuous image of the opposing area of liquid-crystal light valves 12a on a photocell 23, 25, 27, 29, and 31 below it. The image from the lens 22 represents the range of wavelengths to which only the blue-sensitive layer is sensitive. The lens 24 images the range of overlap between blue and green onto the photocell 25. The lens 26 accounts for the pure green range, the lens 28 the overlap between green and red, and the lens 30 the pure red.

This embodiment is intended for the sequentially double exploitation of the sensors for the overlapping ranges. The apparatus operates in the following manner: The translucency of the light valves 12a' above lenses 22 and 24 is controlled in accordance with the sensitivity curve B, with photocells 23 and 25 together issuing the weighted blue. The result is stored in the processor 18'. At the same time, the valves above the lenses 28 and 30 are controlled in accordance with the red sensitivity curve, and photocells 29 and 31 supply the weighted red to the processor. Subsequently thereafter, the light valves 12a above the lenses 24, 26, and 28 are adjusted to the green curve in FIG. 2a, and the photocells 25, 27, and 29 supply the total intensity weighted with the green component to the processor 18'. Although this system takes twice as much time for evaluation, it has the advantage that the light valves 12a can be ideally positioned in accordance with the intensity distribution of the spectrum.

Figure 5:
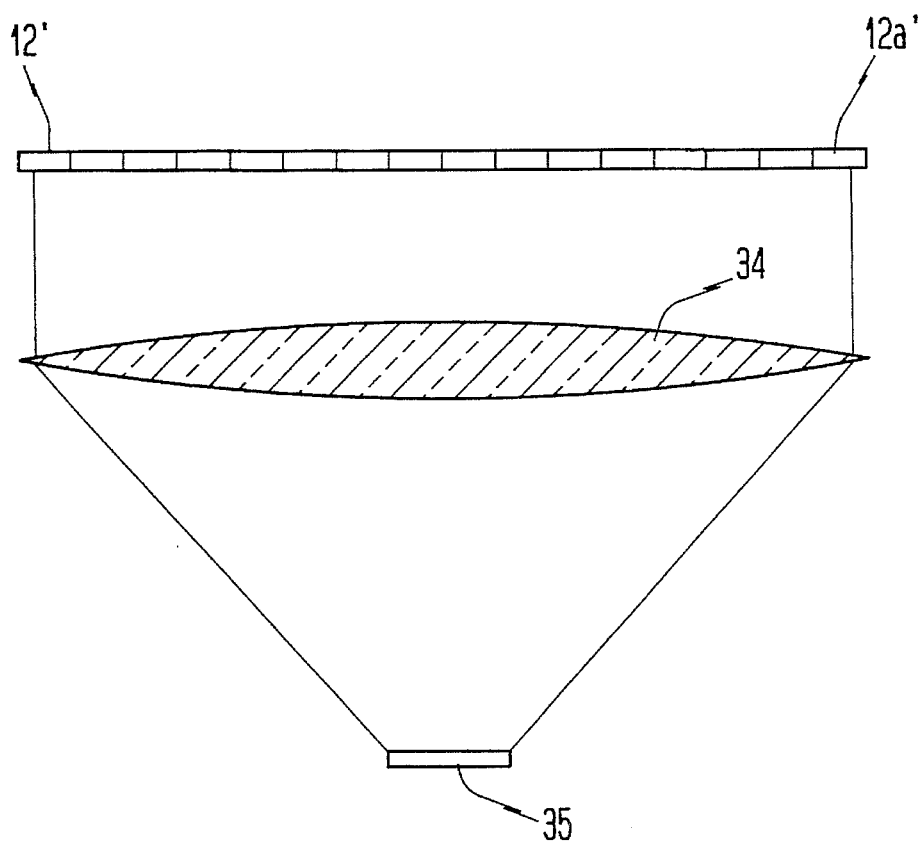
FIG. 5 is a front view of still another distribution arrangement with a single light collection device for measuring light emerging from a single light valve row.

Another version, in accordance with FIG. 5, that differs slightly from the one illustrated in FIG. 3 has only one ocular lens 34 for the whole row of light valves and one photocell 35 intercepting all the light that travels through the light valves. The three measurement results for blue, green and red, respectively from each area of the negative are obtained sequentially in the following manner: The liquid-crystal light valves 12a' in the wavelength range of blue sensitivity are initially adjusted to the blue curve and the others are rendered opaque (switched off). The light is then passed through the light valves to the single photocell 35. Thereafter, the liquid-crystal light valves in the wavelength range of the green sensitivity curve are switched on and controlled in accordance with this curve to carry out measurements for the green light. Finally, the liquid-crystal light valves in the wavelength range of the red-sensitivity curve are controlled in accordance with that curve and the red light in the given area of the negative is measured. The same procedure is then carried out for each area of the negative in succession.

The results are then processed as described in the aforementioned German Patent No. 2,840,287 (and corresponding U.S. Pat. No. 4,279,502).

There has thus been shown and described a novel method and apparatus for measuring the optical density of a negative which fulfill all the objects and advantages sought therefor. Many changes, modifications, variations and other uses and applications of the subject invention will, however, become apparent to those skilled in the art after considering this specification and the accompanying drawings which disclose the preferred embodiments thereof. All such changes, modifications, variations and other uses and applications which do not depart from the spirit and scope of the invention are deemed to be covered by the invention, which is to be limited only by the claims which follow.

What is claimed is:

1. In a method of measuring the optical density of an original, especially a three-color negative, from which photographic prints to be made, to determine how much printing light of each color penetrates the original when the image thereof is projected onto a color print medium that is sensitive to these colors, wherein the spectral sensitivity of the measuring apparatus is adjusted to that of the print medium and wherein measuring light passes through the original and is resolved into at least one spectrum and the intensities of the light at the various ranges of wavelength are weighted and totaled in accordance with the spectral sensitivity of the particular print medium, the improvement comprising the steps of (1) attenuating light with a plurality of light valves disposed along the spectrum and controlled in accordance with the sensitivity of the print medium to the respective spectral wavelengths, and (2) measuring the resulting weighted intensities of the light at each color that is passed through the light valves by collecting light from a plurality of said light valves with a common photosensor.

2. The method defined in claim 1, wherein any irregularities in the wavelength distribution of the measuring light and in the collection of light behind the light valves are compensated by controlling the attenuation of the light valves in accordance with these irregularities.

3. The method defined in claim 1, wherein, at light wavelength ranges where the print medium is noticeably sensitive to light of two colors, the measuring step comprises measuring the intensities of said two colors of light in temporal succession along the overlapping wavelength range by successive readjustment of the attenuation of the light valves.

4. The method defined in claim 1, wherein the weighted intensities of each color are measured by a photosensor which receives light through a row of controllable light valves associated with that color, said rows of light valves being arranged in adjacent overlapping relationship.

5. Apparatus for measuring the optical density of an original, especially a color negative, from which photographic prints are made to determine how much printing light of each color penetrates the original when an image thereof is projected onto a color print medium that is sensitive to these colors, wherein the spectral sensitivity of the apparatus is adjusted to that of the print medium, said apparatus comprising:

(a) a light source for projecting a measuring light through the original;

(b) an aperture for limiting the area in which light is passed through the original;

(c) a spectroscope for resolving the light passed through the original into a spectrum;

(d) a plurality of light valves for attenuating the spectrally separated light in accordance with the spectral sensitivity of the print medium at a plurality of positions along the spectrum; and (e) at least one photosensor for producing a signal representative of the intensity of light passed through a plurality of said light valves, whereby the intensities of light at the various ranges of wavelength are weighted and may be totaled in accordance with the spectral sensitivity of the particular print medium.

6. The apparatus defined in claim 5, wherein said at least one photosensor includes one photocell for each color.

7. The apparatus defined in claim 6, further comprising means for advancing a strip of originals and wherein said aperture comprises an elongate slit arranged perpendicular to the direction of the advancing strip, and a rotating element for passing light through the original in a defined area that sweeps over the slit across the width of the image area of the original.

8. The apparatus defined-in claim 6, further comprising a plurality of ocular lenses that focus the light leaving the light valves on the photocells associated with each color.

9. The apparatus defined in claim 5, wherein said at least one photosensor includes an uninterrupted series of photocells, each one as long as the range of wavelengths that represent one color, and each one positioned to receive light from a plurality of said light valves.

10. The apparatus defined in claim 5, comprising a plurality of light valves arranged in parallel, the number of the light valves being equal to the number of areas of the original to be separately sensed to simultaneously sense such original at the slit.

11. The apparatus defined in claim 5, further comprising means for controlling the translucency of the light valves in accordance with the desired spectral sensitivity.

12. The apparatus defined in claim 5, further comprising means for controlling said light valves in a bi-stable fashion to render the light valves alternatively translucent and opaque with a controlled duty cycle.

13. The apparatus defined in claim 5, wherein said light valves include a plurality of light valve elements each associated with a particular range of color, said elements associated with one color range being laterally displaced in the plane of the color spectra with respect to elements associated with an overlapping color range, thereby allowing coverage of all the print medium's color sensitivity ranges.

14. The apparatus defined in claim 5, wherein said at least one photosensor includes a plurality of photocells, one for each color and one for each color overlap in the color sensitivity range of the print medium, and means for sequentially controlling the light valves for passing light in accordance with the spectral sensitivity of the print medium to the overlapped colors.

15. The apparatus defined in claim 5, comprising a single row of light valves arranged to cover the entire range of spectral sensitivity of the print medium; a single photocell arranged to receive light passed through said row, and light valve control means for successively adjusting the light valves in accordance with the blue, green, and red sensitivity curves of the print medium, respectively, thereby to successively measure the light intensities for each color.

16. The apparatus defined in claim 5, further comprising means for controlling the light valves to compensate for any irregularities in the wavelength distribution of the measuring light.

17. The apparatus defined in claim 5, comprising a single row of light valves arranged to cover the entire range of spectral sensitivity of the print medium; and comprising means for measuring the intensities of two colors of light in temporal succession along an overlapping wavelength range by successive readjustment of the attenuation of the light valves.

18. The apparatus defined in claim 5, further comprising means for controlling the light valves to compensate for any irregularities in the collection of light behind the light valves.

19. In a method of measuring the optical density of an original, especially a three-color negative, from which photographic prints to be made, to determine how much printing light of each color penetrates the original when the image thereof is projected onto a color print medium that is sensitive to these colors, wherein the spectral sensitivity of the measuring apparatus is adjusted to that of the print medium and wherein measuring light passes through the original and is resolved into at least one spectrum and the intensities of the light at the various ranges of wavelength are weighted and totaled in accordance with the spectral sensitivity of the particular print medium, the improvement comprising the steps of (1) attenuating light with a plurality of light valves disposed along the spectrum and controlled in accordance with the sensitivity of the print medium to the respective spectral wavelengths, (2) collecting and measuring the resulting weighted intensities of the light at each color that is passed through the light valves; and (3) compensating any irregularities in the wavelength distribution of the measuring light and in the collection of light behind the light valves by controlling the attenuation of the light valves in accordance with these irregularities.

* * * * *